United States Patent
Hajime et al.

(10) Patent No.: US 9,921,199 B2
(45) Date of Patent: Mar. 20, 2018

(54) METHOD FOR INDICATING MOISTURE BASED ON BIS(GLYOXIME)-TRANSITION METAL COMPLEXES

(71) Applicant: 3M INNOVATIVE PROPERTIES COMPANY, St. Paul, MN (US)

(72) Inventors: Evan Koon Lun Yuuji Hajime, Woodbury, MN (US); Myungchan Kang, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 35 days.

(21) Appl. No.: 15/153,076

(22) Filed: May 12, 2016

(65) Prior Publication Data

US 2016/0258915 A1    Sep. 8, 2016

Related U.S. Application Data

(62) Division of application No. 14/008,141, filed as application No. PCT/US2012/030677 on Mar. 27, 2012.

(Continued)

(51) Int. Cl.
*G01N 21/00* (2006.01)
*G01N 31/22* (2006.01)
(Continued)

(52) U.S. Cl.
CPC .......... *G01N 31/222* (2013.01); *G01N 21/81* (2013.01); *G01N 31/22* (2013.01); *G01N 2021/758* (2013.01); *G01N 2021/7773* (2013.01)

(58) Field of Classification Search
CPC .................................................. G01N 31/222
(Continued)

(56) References Cited

U.S. PATENT DOCUMENTS

| 2,460,068 A | 1/1949 | Bell |
|---|---|---|
| 2,460,074 A | 1/1949 | Bell |

(Continued)

FOREIGN PATENT DOCUMENTS

| GB | 1271338 | 4/1972 |
|---|---|---|
| GB | 2368908 | 5/2002 |

(Continued)

OTHER PUBLICATIONS

"CIE 1931 color space", Wikipedia, [retrieved from the internet on Sep. 18, 2006], URL <http://en.wikipedia.org/wiki/CIE_color_space>, 8pgs.

(Continued)

*Primary Examiner* — Christine T Mui
*Assistant Examiner* — Emily R. Berkeley
(74) *Attorney, Agent, or Firm* — Qiang Han

(57) ABSTRACT

Compositions that include bis(glyoxime)-transition metal complexes bound to metal oxide solid supports are provided. In some embodiments the compositions include nickel dimethylglyoxime and the metal oxide supports can be alumina or silica. These compositions can be used to make a colorimetric moisture-indicating sensor that changes visible reflection spectrum quantitatively and reversibly according to the amount of moisture in contact with the sensor. Also provided is a method of detecting moisture using the provided compositions.

5 Claims, 3 Drawing Sheets

Related U.S. Application Data

(60) Provisional application No. 61/470,078, filed on Mar. 31, 2011.

(51) Int. Cl.
   *G01N 21/81* (2006.01)
   *G01N 21/75* (2006.01)
   *G01N 21/77* (2006.01)

(58) Field of Classification Search
   USPC .......................................................... 436/164
   See application file for complete search history.

(56) References Cited

U.S. PATENT DOCUMENTS

| | | | |
|---|---|---|---|
| 2,580,737 | A | 1/1952 | Bell |
| 3,216,802 | A | 11/1965 | Smith, Jr. |
| 3,607,782 | A | 9/1971 | Rosen |
| 5,028,395 | A | 7/1991 | Sebille et al. |
| 5,064,576 | A | 11/1991 | Suto |
| 5,224,373 | A * | 7/1993 | Williams ............ G01N 31/222 73/29.02 |
| 5,320,969 | A | 6/1994 | Bauer |
| 6,698,378 | B1 | 3/2004 | Dick |
| 7,098,253 | B2 | 8/2006 | Rasmussen |
| 7,314,582 | B1 | 1/2008 | Beitz |
| 7,553,450 | B2 | 6/2009 | Attar |
| 7,674,835 | B2 | 3/2010 | Rasmussen |
| 7,683,100 | B2 | 3/2010 | Rasmussen |
| 2003/0056710 | A1 | 3/2003 | Radmacher |
| 2005/0274055 | A1 | 12/2005 | Cook |
| 2006/0154414 | A1 | 7/2006 | Lin |
| 2008/0163673 | A1 | 7/2008 | Attar |
| 2009/0035865 | A1 | 2/2009 | Demoor |
| 2012/0062892 | A1 * | 3/2012 | Wendland ............ G01N 21/77 356/405 |

FOREIGN PATENT DOCUMENTS

| | | |
|---|---|---|
| JP | S51-5097 A | 1/1976 |
| JP | H03-65639 A | 3/1991 |
| JP | H04-501319 T | 3/1992 |
| JP | H06-336509 A | 12/1994 |
| JP | 2006-326221 | 12/2006 |
| JP | 2007-322345 | 12/2007 |
| JP | 2007-327887 A | 12/2007 |
| JP | 2008-216147 A | 9/2008 |
| JP | 2008-224461 A | 9/2008 |
| JP | 6023745 | 10/2016 |
| WO | WO 91/02973 A1 | 3/1991 |
| WO | WO 2001-09601 | 2/2001 |
| WO | WO 2004-099754 | 11/2004 |
| WO | WO 2012-154314 | 11/2012 |

OTHER PUBLICATIONS

"Hue", Wikipedia, [retrieved from the internet on Mar. 29, 2011], URL <http://en.wikipedia.org/wiki/Hue>, 1 pg.
Bambenek, "The Reaction of Nickel with Dioximes", Inorganic Chemistry, 1963, vol. 2, No. 2, pp. 289-292.
International Search Report for PCT International Application No. PCT/US2012/065022, dated Feb. 27, 2013, 4pgs.
International Search Report for PCT International Application No. PCT/US2012/030677, dated Jul. 24, 2012, 4 pgs.
Mackenzie, "Inorganic polymers (geopolymers) containing acid-base indicators as possible colour-change humidity indicators", Materials Letters, 2009, vol. 63, pp. 230-232.
Mitchell, "Colorimetric Determination of Nickel with Dimethylglyoxime", Industrial and Engineering Chemistry, 1945, vol. 17, No. 6, pp. 380-382.
Négrier et. al., A Systematic Study of the Interactions between Chemical Partners (Metal, Ligands, Counterions, and Support) Involved in the Design of $Al_2O_3$-Supported Nickel Catalysts from Diamine—Ni(II) Chelates, J. Phys. Chem. B, vol. 109, No. 7, 2005, 10 pages.
Ozkan, "Synthesis of New Glyoxime Derivatives, Characterization and Investigation of Their Complex with Co(II), Ni(II), and Cu(II) Metals and Thermal Studies", Russian Journal of Coordination Chemistry, 2005, vol. 31, No. 7, pp. 506-510.
Walker, "Colour Rendering of Spectra", Apr. 25, 1996, 7pgs.
Yasuda, "Photofunctional Silica Gel Beads as Environmental Conscious Materials", Journal of Synthetic Organic Chemistry, 2010, vol. 68, No. 3, pp. 238-246.
Yu. G. Silzhov and M.A. Gavrilenko, "Gas-Chromatographic Properties of Silochrom with a Surface Layer of Nickel Dimethylglyoximate and Acetylacetonate Complexes", Journal of Analytical Chemistry, vol. 56, No. 6, 2001, pp. 538-541.
Balkose, "Dynamics of water vapor adsorption on humidity-indicating silica gel" Applied Surface Science, 1998, vol. 134, pp. 39-46.

* cited by examiner

METHOD FOR INDICATING MOISTURE BASED ON BIS(GLYOXIME)-TRANSITION METAL COMPLEXES

FIELD

The present disclosure relates to moisture indicators that include bis(glyoxime)-transition metal complexes.

BACKGROUND

Moisture indicators are used, for example, to determine the amount of moisture or humidity in the vicinity of the indicator. One type of moisture indicator changes color upon exposure to moisture or humidity. In some embodiments, colorimetric moisture indicators change color reversibly when exposed to moisture or humidity and will revert to their original color upon removal from this exposure. In other embodiments, colorimetric moisture indicators change color irreversibly so that after initial exposure to moisture or humidity the indicator remains colored and does not reversibly change back to its original color state.

Cobalt chloride has been widely used as a moisture-indicating medium. For example, the use of cobalt chloride for determining the moisture content of paper has been disclosed. Silica gel-supports that include iron (II) or iron (III) salts or with copper chloride have also been used as moisture indicators. Also lanthanide-halide based humidity indicators have been disclosed wherein an adsorbent support such as silica gel is impregnated with, for example, europium halide salts. However, cobalt and lanthanides are expensive and cobalt has some environmental concerns. Supports with iron salts or copper chloride do not show strong absorptions in the visible electromagnetic spectrum and are hard to detect.

SUMMARY

There is a need for colorimetric moisture indicators that are not based on cobalt and that are economical. There is also a need for colorimetric moisture indicators that have a highly visible color across a wide range of humidity levels and that can change qualitatively and/or quantitatively with a change in humidity.

In one aspect a composition is provided that includes a solid metal oxide support and
a bis(glyoxime)-transition metal complex bound to the support. The solid metal oxide support can include an oxide of aluminum, silicon, or a combination thereof. The bis(glyoxime)-transition metal complex can have a square planar configuration and, in some embodiments, the transition metal can include nickel, copper, rhodium, iridium, platinum, palladium, gold, or a combination thereof.

In another aspect, a colorimetric moisture-indicating sensor is provided that includes a solid metal oxide support and a bis(glyoxime)-transition metal complex bound to the support. The visible spectroscopic reflection spectrum of the moisture-indicating sensor changes quantitatively and reversibly according to the amount of moisture in contact with the sensor. The solid metal oxide support can be selected from aluminum oxide and silicon oxide. In some embodiments, the transition metal is nickel. In these embodiments, the moisture-indicating sensor is reversible and changes color depending upon the amount of moisture in the environment contacting it. In some embodiments, the amount of moisture in contact with the sensor can be determined by measuring the visible spectroscopic reflection spectrum of the sensor. In some embodiments, the intensity change in the visible spectroscopic reflection spectrum can be measured at wavelengths that range from 460 nm to 560 nm. In other embodiments, the visible reflection spectroscopic color intensity change can be expressed by the change in the Hue number obtained from the spectrum.

Finally, in another aspect, a method of detecting moisture is provided that includes providing a composition of a solid metal oxide support and a bis(glyoxime)-transition metal complex bound to the support and then exposing the composition to a moist atmosphere. In some embodiments, the transition metal is nickel. In these embodiments, the visible spectroscopic reflection color intensity change is reversible and dependent upon the amount of moisture in the environment contacting it. In some embodiments, the amount of moisture in contact with the composition can be determined by measuring the visible spectroscopic reflection of the composition. The visible spectroscopic reflection spectrum of the composition can be measured, for example, in the wavelength range of 460 nm to 560 nm. The visible spectroscopic reflection color intensity change of the composition can be quantitative and reversible. The amount of moisture in contact with the composition can also be expressed in Hue number.

In this disclosure:

"bis(glyoxime)-transition metal complex" refers to a complex that has two glyoxime moieties complexed to a transition metal; the glyoxime moieties may have alkyl or other groups substituted for hydrogen at the ortho positions, for example, dialkylglyoximes where alkyl can be methyl, ethyl, or phenyl;

"glyoxime" refers to vicinal dioximes of substituted or unsubstituted orthoketones;

"Hue number" refers to the degree to which a stimulus can be described as similar to or different from stimuli that are described as red, green, and blue and can be calculated using known mathematical techniques described further herein;

"humidity" and "moisture" are used interchangeably;

"visible spectroscopic reflection color intensity change" refers to the difference observed between two color states and can be expressed in difference in Hue number; and "visible spectroscopic reflection " refers to measurements of reflections that are typically in the near UV-visible region of the electromagnetic spectrum—from about 350 nm to about 830 nm; it is understood that the actual reflection spectrum of a particular composition may be influenced by solvent, solvation, interference of thin surface coatings, and other environmental parameters such as temperature.

The provided compositions, sensor, and methods provide an alternative to the use of cobalt-based moisture-indicating sensors. Additionally, the provided sensors and methods can provide reversible and quantitative indications of the amount of moisture in the environment to which the sensor is exposed.

The above summary is not intended to describe each disclosed embodiment of every implementation of the present invention. The brief description of the drawings and the detailed description which follows more particularly exemplify illustrative embodiments.

DETAILED DESCRIPTION

Figure 1:
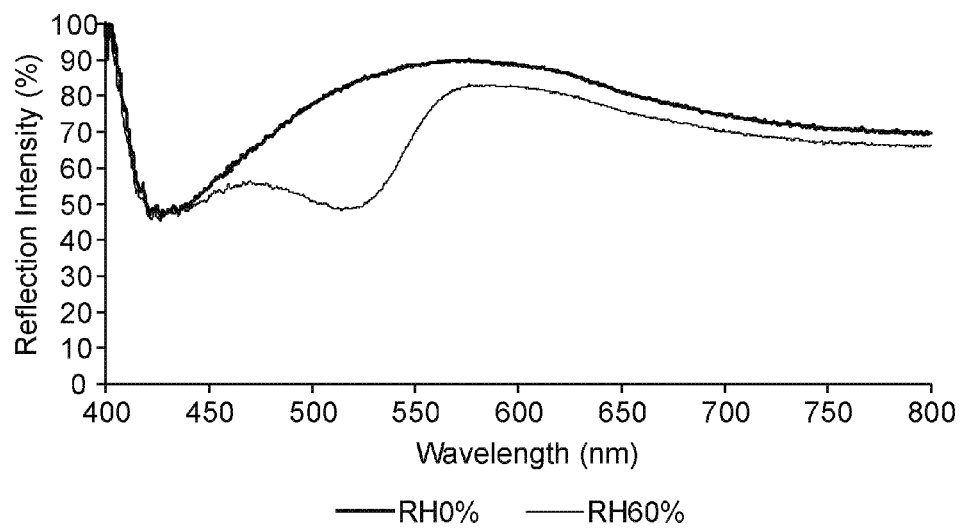
FIG. 1 is a graph of the reflection intensity of the reflection spectrum of an embodiment of the provided moisture indicator at 0% and 60% relative humidity.

In the following description, reference is made to the accompanying set of drawings that form a part of the description hereof and in which are shown by way of illustration several specific embodiments. It is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Current commercially available humidity indicator cards (HICs) rely on inorganic salts such as cobalt (II) chloride to provide visual indication by color intensity change upon exposure to various levels of relative humidity (RH). There are a variety of commercially available HICs that contain an array of humidity sensors (typically appearing as spots) calibrated for various RH levels, but generally each humidity sensor spot makes use of the same chemistry. Spots that are designed to indicate low RH typically make use of just a small amount of the indication chemistry, and as a result, the color tends to be very pale. Another problem with the use of inorganic salts for humidity indication is that the color intensity change (for example, blue to pink for cobalt (II) chloride) can be difficult to ascertain, and hence determine the humidity exposure level.

Cobalt (II) chloride is typically used in commercial HICs. Recently, cobalt (II) chloride has come under regulatory scrutiny. Compositions that include a solid metal oxide support and a bis(glyoxime)-transition metal complex bound to the support can be used for colorimetric moisture or humidity determination. Depending upon composition, humidity sensors can be constructed which can quantitatively and reversibly determine the humidity level of the atmosphere to which the sensor is exposed. In other embodiments, the provided compositions can be used to irreversibly determine humidity.

Compositions are provided that include a solid metal oxide support. The provided solid metal oxide support can be relatively colorless and capable of adsorbing or bonding to chromophoric species. In some embodiments, the provided solid metal oxide supports include oxides of silicon, aluminum, or combinations thereof. Inorganic polymers (geopolymers) formed by reaction of a reactive solid aluminosilicate source such as a dehydroxylated clay with alkali silicate solution containing acid-base indicators as possible color-changing humidity indicators have been disclosed, for example, in MacKenzie et al., *Materials Letters*, 63, 230-232 (2009). In other embodiments, the provided solid metal oxide supports can include alumina or silica gels, beads, or solid supports. Additional exemplary support types include polymers such as ion-exchange resins, carbonate, sulfate, phosphate, and hydroxide supports. Additional metal oxide materials that can be used in the provided compositions, sensors and methods include titania and zirconia.

The provided compositions include a bis(glyoxime)-transition metal complex bound to the support. By bound it is meant that there is an attractive interaction between the bis(glyoxime)-transition metal complex and the solid metal oxide support. The attractive interaction can include covalent bonds, ionic bonds, dative bonds, metallic bonds, hydrogen bonds, van der Waals forces, electrostatic forces, chemisorption, physisorption, or any other interaction that attracts the bis(glyoxime)-transition metal complex to the solid metal oxide support. Typically when a bis(glyoxime)-transition metal complex is bound to a solid metal oxide support, it is not removed by successive or continuous rinsing with a solvent of the complex.

The bis(glyoxime)-transition metal complex includes two glyoxime moieties that form a complex with transition metals. Common glyoxime moieties include dialkylglyoximes such as, for example, dimethylglyoxime and diethylglyoxime. Common glyoximes that may also be useful in the provided compositions include diphenylglyoxime and bis(thiophenyl)glyoxime. Additionally, morpholine and piperidine have been reacted with anti-chloroglyoxime to give morpholineglyoxime and piperidineglyoxime. Since the transition metal ion complexes with the heteroatoms of the glyoxime species (nitrogen and oxygen, for example) it is contemplated that other substituents on the glyoxime molecule may be useful compositions if they do not interfere with the ability of the two glyoxime moieties to complex with a transition metal ion. When complexed, the bis(glyoxime)-transition metal complex typically has a square planar configuration. The bis(glyoxime)-transition metal complex can include ions of rhodium, iridium, platinum, palladium, gold, nickel or copper which are well known by those of ordinary skill in the art to form square planar coordination complexes with glyoxime moieties like dimethylglyoxime. A structure of an exemplary nickel bis(dimethylglyoxime) complex, bis-(dimethylglyoximato) nickel (II), is shown in Structure (I) below:

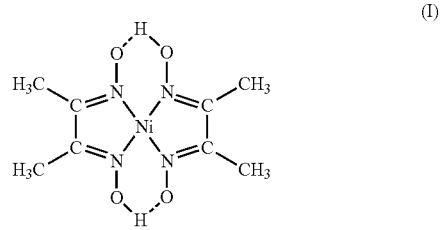

(I)

Using some of the above-identified compositions, colorimetric moisture-indicating sensors can be constructed. For example, when the solid metal oxide support is aluminum oxide, silicon oxide, or a combination thereof, and when the bis(glyoxime)-transition metal complex includes nickel and two dimethylglyoxime moieties (the complex shown in Structure (I)) a reversible colorimetric moisture-indicating sensor can be formed.

The color of the embodied moisture-indicating sensor can change quantitatively and reversibly according to the amount of moisture (or humidity) in contact with the sensor. For example, a provided composition that includes bis (glyoxime)-transition metal complex (bis-(dimethylglyoximato)-nickel (II)) has a strong absorption at wavelengths from about 460 nm to about 570 nm with a peak at a wavelength of around 520 nm. The visible absorbance peaks or reflection valleys of many other bis(glyoxime)-transition metal complexes having a square planar configuration are well known.

The amount of moisture to which the colorimetric moisture-sensor is exposed can be measured spectroscopically, for example, by reflection. Since the provided colorimetric moisture-indicating sensor is a solid, the change in color can be measured by reflecting light off of the surface of the solid and measuring the loss of intensity from wavelengths absorbed by the surface. In some embodiments, the absorbance at a given wavelength can be measured using an optics spectroscopy system that is configured for reflection spectroscopy. An exemplary optics spectroscopy system suitable for this measurement is Model Jaz-EL350, available from Ocean Optics, Dunedin, FL. Typically, a spectrum from a white piece of paper can be used as a reference spectrum when measuring reflection intensity.

Also provided is a method of detecting moisture. The method includes providing a composition that includes a solid metal oxide support and a bis(glyoxime)-transition metal complex bound to the support and then exposing the composition to a moist atmosphere. The visible spectroscopic reflection intensity in the wavelength range of 460 nm to 560 nm and color, which is expressed to the Hue number, of the composition changes quantitatively and reversibly according to the amount of moisture (humidity or relative humidity) in contact with the composition. By quantitatively it is meant that the reflection intensity in the wavelength range of 460 nm to 560 nm and the Hue number, expressed by color, has a one-to-one correlation to the amount of humidity. By reversible it is meant that when the composition is exposed to one set of humidity conditions it has a specific absorption. When the set of humidity conditions is changed, the composition changes color to give a different specific reflection spectrum. And, when the composition is returned to the initial set of humidity conditions, the spectroscopic reflection spectrum (or color) returns to the original specific absorption. The provided method further includes measuring the visible spectroscopic reflection spectrum of the composition exposing it to a moist atmosphere.

Objects and advantages of this invention are further illustrated by the following examples, but the particular materials and amounts thereof recited in these examples, as well as other conditions and details, should not be construed to unduly limit this invention.

EXAMPLES

Example 1

Preparation of Nickel-Dimethylglyoxime-Alumina ($Ni^{2+}$-dmg/$Al_2O_3$ spheres) System Alumina beads (SASOL Germany GmbH, Alumina Spheres 1,8/210, 207 $m^2/g$, 1.8 mm diameter spherical beads) (3.78 g) were immersed in a 0.1 M nickel acetate tetrahydrate aqueous solution (10.38 g), and the mixture was mixed by turning in a jar for more than one hour. The supernatant was then decanted, and the light green colored beads were then washed with deionized water, repeating the decant-wash cycle several times until the solution remained colorless. After several decant-water wash cycles to remove residual free nickel ion from the reaction vessel, 2.93 g of (16.4 mM dimethylglyoxime/0.17 M potassium hydroxide (aq)) solution was quickly added to the vial containing the beads. The beads and solution rapidly changed to a red color, and the mixture was further shaken by hand for two minutes before decanting and washing the beads several times to remove any species not strongly adsorbed on the alumina. The mixture was vacuum filtered in a Buchner funnel (WHATMAN® filter paper #5) and the red colored beads were collected and dried on a glass dish at 70° C. under dynamic vacuum overnight (~16.5 hours). The resulting beads were uniformly light yellow-green in color and weighed 4.00 g.

Humidity Control and Optical Measurements

The color intensity changes at various humidity levels were observed using an ocean optics spectroscopy system (available from Ocean optics, Model Jaz) and a digital camera (available from Sony, Model DSC-S85 with Tiffen close-up lenses 43mm +10 close-up and 43mm+7 close-up in series). The humidity was generated by passing dry air flow over a 500 ml temperature controlled water jacketed flask. The air stream of dry airwas regulated by a Matheson gas flow meter. Around 250 ml of distilled water was contained in the flask and dry air was delivered to evaporate water. Proper humidity was generated by controlling the temperature of circulating water which was connected to a Heating/Cooling Circulator (available from VWR, Model 1160S). In order to obtain step changes of humidity level, humid air and dry air were mixed. TEFLON tubing was used throughout the delivery system. The humidity and temperature was monitored and recorded with an iTHX-M Humidity Meter (available from Omega Engineering Inc. of Stamford, Conn.). Dry or humid air was introduced to a test chamber made of two glass plates and rubber spacers.

The $Ni^{2+}$-dmg/$Al_2O_3$ spheres were held between glass fibers inside the chamber. The ocean optics optical probe was located above the spheres to measure reflection spectra. A spectrum from a piece of white paper was used for a reference spectrum for reflection intensity. The wavelength range of spectra was from 340.58nm to 1031.1 nm. Humidity, temperature, and reflection spectra were simultaneously obtained. The obtained reflection spectrum was converted to color (Hue number) as follows. The measured reflection spectrum was constructed to CIE XYZ color space using color matching matching CIE 1931 2° Standard Observer function. The CIE XYZ color space was linear transformed to National Television System Committee (NTSC) RGB space using NTSC color space chromaticity coordinates ($x_R$=0.67, $y_R$=0.33. $x_G$=0.21, $y_G$=0.71, $x_B$=0.14, $y_B$=0.08). Then, Hue number which is one of the main properties of a color, was computed from RGB values. Hue is defined as the degree to which a stimulus can be described as similar to or different from stimuli that are described as red, green, and blue. The color can be correlated to a location (Hue) in the color wheel from 0 degree to 360 degree. All mathematical process was done by a customized LABVIEW program (software available from National Instruments of Austin, Tex.). The conversion from spectra to Hue number was confirmed by measuring spectra from color printed papers with known Hue numbers, calculating Hue numbers from spectra and comparing Hue numbers from spectra with the known Hue numbers of standard color printed papers. Hue numbers from spectra were consistent with the known Hue numbers of standard color printed papers.

Example 2

Preparation of Copper-Dimethylglyoxime-Silica Glass System

A copper-dimethylglyoxime solution containing 0.74 g of the supernatant solution of "saturated", basic dimethylglyoxime (3.75 g dimethylglyoxime+14.80 g 1 M potassium hydroxide+69.54 g deionized water) and 2.05 g of 5 wt % copper sulfate pentahydrate aqueous solution was prepared by direct mixing of the separate aqueous solutions.

A drop of the copper-dimethylglyoxime solution was cast onto a glass microscope slide and dried for 10 minutes at 70° C. in air. The dried drop was light green in color, and half of the dried drop was immediately covered with transparent pressure sensitive adhesive tape. The entire glass slide was then immersed in an atmosphere of 94% relative humidity at 22° C. (vessel containing equilibrated, saturated potassium nitrate aqueous solution) for 12.5 minutes. The covered part of the dried drop remained light green in color, while the exposed portion changed in color to a yellow-brown. Reheating the slide at 70° C. in air did not appear to regenerate the light green color.

Example 3

Preparation of Nickel-Dimethylglyoxime-Aluminosilicate System 41.67 g of Aluminosilicate 4A molecular sieve beads (Alfa Aesar, Molecular sieves, 4A, 1-2mm) were mixed with nickel(II) acetate tetrahydrate (4.08 g) and deionized water (50.11 g), and the mixture was jar rolled for 1 hour to give a mixture of very light green solids and light green solution. The beads were vacuum filtered and washed with water before drying several days in air at 75° C. The dried beads were added directly to a basic, aqueous solution of dimethylglyoxime (0.76 g dimethylglyoxime, 14.36 g 1M potassium hydroxide (aq), 77.85 g deionized water) resulting in a rapid color intensity change to a red color upon immersion into solution. The mixture was then jar rolled overnight to give a mixture of red fine particles, red molecular sieve beads and red colored solution. The mixture was vacuum filtered (WHATMAN® #5 filter paper) and washed once with water. The red colored beads were collected and placed in a glass dish to dry overnight in air at 75° C. After drying, the beads lost significant intensity of red coloration, and contained a mixture of yellow to red colored beads.

Example 4

Preparation of Nickel-Dimethylglyoxime-Silica System

Silica gel 60 (Alfa Aesar, 150-230 mesh, 500-600 m²/g) (1.80 g) was immersed in 5 wt% nickel acetate tetrahydrate aqueous solution (7.62 g) and allowed to sit for one hour. The silica gel was then vacuum filtered over a WHATMAN® #5 filter paper and thoroughly washed with deionized water to remove residual, free nickel ions in solution. The damp, white beads were then transferred to a glass vial followed by the rapid addition of 5.53 g of basic, dimethylglyoxime solution (0.11g diphenylglyoxime, 10.39 g 1M potassium hydroxide, 47.38 g deionized water). The gel particles and solution quickly changed to a red color, and after two minutes of mixing, the mixture were vacuum filtered over a WHATMAN® #5 filter paper and washed with deionized water. During washing, free floating nickel dimethylglyoxime surface films were carefully removed from the surface of the water over the beads to minimize mixing of the nickel dimethylglyoxime residues and the nickel dimethylglyoxime impregnated silica gel. After allowing the gel particles to partially dry on the filter under vacuum suction, the partially damp beads were further dried in a vacuum oven at 70° C. overnight (~16.5 hrs) in air. The resulting dried gel beads were yellow in color.

Example 5

Preparation of Nickel-Diphenylglyoxime-Alumina System

Alumina beads (SASOL Germany GmbH, Alumina Spheres, 207 m²/g, 1.8 mm diameter spherical beads) (3.51 g) were immersed in 5 wt % nickel acetate tetrahydrate aqueous solution (8.54 g) and allowed to sit for one hour. The supernatant was then decanted and the light green colored beads were washed with deionized water. Several decant and wash cycles were performed to remove residual, free nickel ions in solution before the rapid addition of 11.12 g of basic, diphenylglyoxime solution (0.07 g diphenylglyoxime, 4.87 g 1M potassium hydroxide, 15.10 g deionized water). An orange colored solution quickly formed above the beads, and after five minutes of mixing by hand, the beads changed from a light green color to an orange color. Several decant wash cycles were again performed to remove soluble species and residual nickel diphenylglyoxime particles, and the wet beads were then dried in a vacuum oven at 70° C. overnight (~16.5 hrs) in air. The resulting dried beads were uniformly dark yellow in color.

Examples 6-12

General Procedure

The support material (see Table 1) was immersed for 10-15 minutes in an aqueous 5 wt % nickel acetate tetrahydrate solution, followed by deionized water washing and decanting cycles (at least 3 times) in a small 10 mL glass vial until the supernatant solution was colorless. After final decanting, a small amount of dimethylglyoxime (dmg) solution (Formulation: 0.12 g dimethylglyoxime+11.54 g 1M potassium hydroxide (aq) +28.34 g deionized water) was added to the vial, and the mixture was mixed for 30-120 seconds before water washing/decant cycles were performed (at least 3 cycles) in small 10 mL glass vial until the supernatant solution was colorless. The wet solids were then transferred to a small glass Petri dish, and allowed to dry in an oven at 110° C. between 15-3960 minutes in air. More details for specific supports are found in Table 2 below.

TABLE 1

Materials for Examples 6-12

| Example | Support | Supplier Details | Support Type |
|---|---|---|---|
| 6 | AMBERLITE IRC-50 C.P. ion exchange resin, weakly acidic, carbonxylic (polymethacrlic) | Mallinckrodt Chemical Works | Polymeric (carboxylated, weakly acidic) |

TABLE 1-continued

Materials for Examples 6-12

| Example | Support | Supplier Details | Support Type |
|---|---|---|---|
|  | type cation exchange resin - medium porosity |  |  |
| 7 | AMBERLYST −15 ion exchange resin, strongly acidic, macroreticular resin with sulfonic functionality | Sigma-Aldrich, Stock#216380 | Polymeric (sulfonated, strongly acidic) |
| 8 | DRIERITE 100% anhydrous calcium sulfate, 8 mesh | W.A. Hammond Drierite Co. Ltd., Stock#13005 | Sulfate |
| 9 | Zinc Carbonate Hydroxide, Reagent Grade | Alfa Aesar, Stock#33398, Lot#D01M42 | Carbonate, Hydroxide |
| 10 | Calcium Phosphate, Monobasic, Purified Grade | Fisher Scientific Co., Stock#C-121, Lot#724573 | Phosphate |
| 11 | Zirconium oxide, 1/8" pellets, catalyst support, 99% | Alfa Aesar, Stock#43814, Lot#G11L41 | Metal oxide |
| 12 | Titanium (IV) oxide, 1/8" pellets, catalyst support | Alfa Aesar, Stock#44429, Lot#K14T044 | Metal oxide |

TABLE 2

Details of Examples 6-12

| Example | Support (g) | Ni soln (g) | Immersion Time (mins) | Dmg soln (g) | Immersion Time (secs) | Drying time (mins) | Wet Color | Dry Color |
|---|---|---|---|---|---|---|---|---|
| 6 | 0.35 | 3.80 | 15 | 2.51 | 30 | 3960 | Bright Pink | Red |
| 7 | 0.10 | 3.25 | 15 | 4.93 | 60 | 3960 | Dark Pink | Grey-Brown |
| 8 | 0.91 | 4.49 | 15 | 2.20 | 30 | 15 | Light Pink | White |
| 9 | 0.50 | 4.37 | 10 | 2.34 | 30 | 20 | Bright Pink | Orange-Pink |
| 10 | 0.82 | 4.77 | 15 | 2.46 | 120 | 120 | Light Pink | White |
| 11 | 1.28 | 3.74 | 15 | 2.44 | 30 | 30 | Pink | Yellow-Pink |
| 12 | 0.76 | 4.66 | 10 | 2.24 | 30 | 30 | Light Pink | Yellow |

Figure 2:
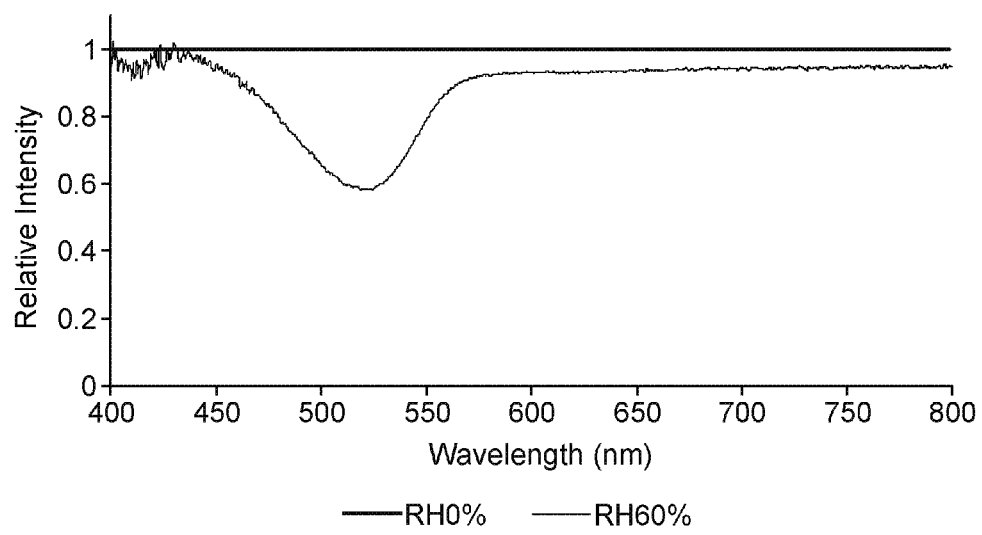
FIG. 2 is a graph of the relative intensity at 0% and 60% relative humidity of the reflection spectrum of FIG. 1.

FIG. 1 is a graph of the reflection spectra of intensity of the exemplary $Ni^{2+}$-dmg/$Al_2O_3$ spheres at RH 0% and RH 60%. FIG. 2 is a graph of the relative intensity spectra with respect to the initial spectrum measured at RH 0%. Relative intensity clearly decreases around the wavelength of 520 nm as the relative humidity increases.

Figure 3A:
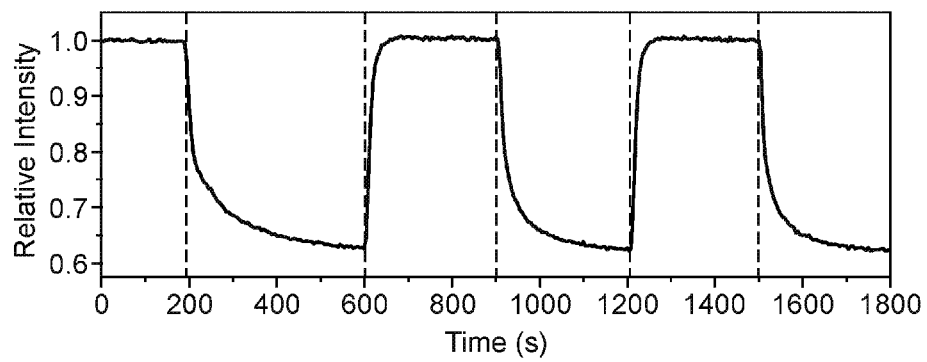
FIGS. 3a-c are graphs of the relative intensity of the reflection spectrum at 520.46 nm, the hue number, and the corresponding relative humidity at 21.7° C., respectively as a function of time for the embodiment shown in FIGS. 1-2 as the relative humidity is alternated from 0% to 60%.
Figure 3B:
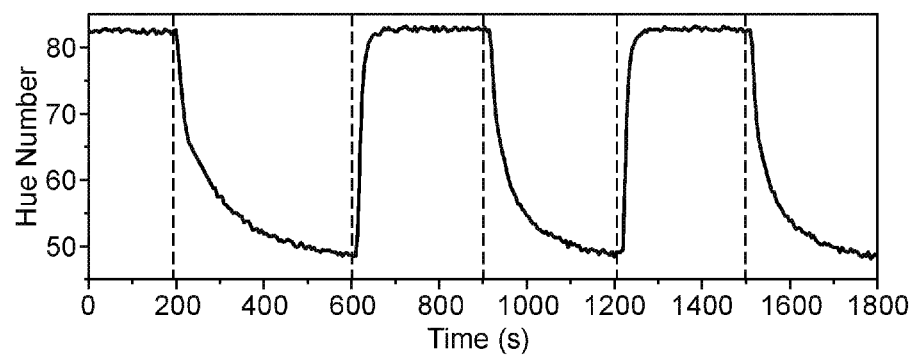
Figure 3C:
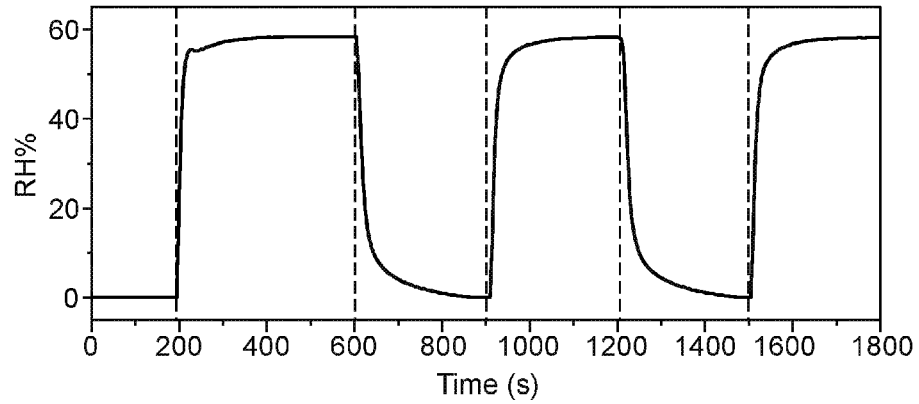

The sample used for FIGS. 1 and 2 was then exposed to periods of 60% RH followed by periods of 0% RH as shown on the graphs in FIG. 3a-3c. FIG. 3a shows the relative intensity of the reflection at 520 nm as a function of time of these samples. FIG. 3b shows the Hue number and FIG. 3c shows the relative humidity as a function of the same time. The changes of relative intensity at 520 nm (FIG. 3a) and Hue number (FIG. 3b) are strongly correlated to the controlled humidity (FIG. 3c). The change of color in $Ni^{2+}$-dmg/$Al_2O_3$ spheres upon humidity exposure is highly reversible and reproducible as shown in FIGS. 3a-3c. The Hue number at RH 0% is around 83 which corresponds to green color and that at RH 60% is around 49 which corresponds to reddish color. The response time to obtain the saturated Hue number at RH 0% and 60% was less than 5 mins as is displayed in the graphs of FIGS. 3a-3c.

Figure 4A:
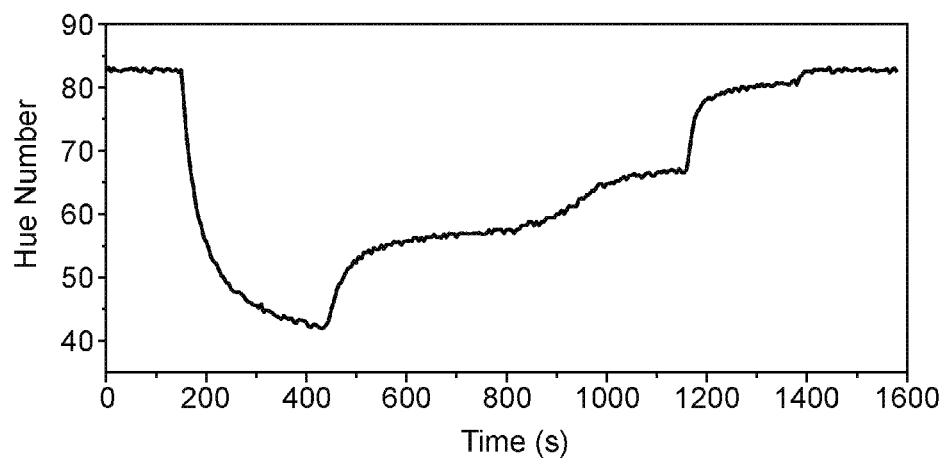
FIGS. 4a and 4b are graphs of the Hue number and relative humidity as a function of time of the same embodiment of the provided moisture indicator.
Figure 4B:
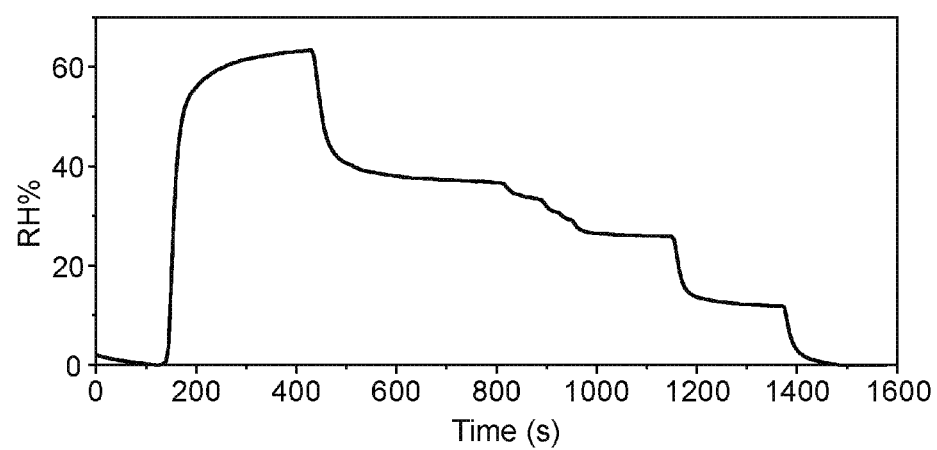

FIGS. 4a and 4b show the change of color with the steps of controlled humidity level. Clear steps of color intensity change were observed at each stepped humidity level. The measured Hue number, indicative of color intensity change is shown in FIG. 4a as a function of exposure time while the corresponding relative humidity is shown as a function of the same exposure time in FIG. 4b. These figures show that the color intensity changes in the $Ni^{2+}$-dmg/$Al_2O_3$ spheres were based on equilibrium among $Ni^{2+}$ complexation ligands such as water, alumina surface, and dmg. Due to the equilibrium at each humidity level, the color expression of $Ni^{2+}$-dmg/$Al_2O_3$ spheres at each humidity level is distinctive.

It was also observed that the color intensity change depends upon the support surface to which the $Ni^{2+}$-dmg ligand was bound. Freshly precipitated, red-colored Ni(dmgH)$_2$ solid (unbound) upon exposure to 60% RH did not result in a color intensity change to light green when the solid was placed on a watch glass in these humidity conditions. $Ni^{2+}$-dmg complexes bound to silica gel surfaces were also found to produce reversible color changing materials.

Following are exemplary embodiments of a bis(glyoxime)-transition metal complexes and moisture indicators made therewith according to aspects of the present invention.

Embodiment 1 is a composition comprising: a solid metal oxide support; and a bis(glyoxime)-transition metal complex bound to the support.

Embodiment 2. A composition according to embodiment 1, wherein the bis(glyoxime)-transition metal complex comprises a bis(dimethylglyoxime)-transition metal complex.

Embodiment 3 is a composition according to embodiment 1, wherein the solid metal oxide support comprises an oxide of aluminum, silicon, or a combination thereof.

Embodiment 4 is a composition according to embodiment 1, wherein the bis(glyoxime)-transition metal complex has square-planar configuration.

Embodiment 5 is a composition according to embodiment 4, wherein the transition metal in the bis(glyoxime)-transition metal complex comprises rhodium, iridium, platinum, palladium, gold, nickel, copper, or a combination thereof.

Embodiment 6 is a composition according to embodiment 5, wherein the transition metal in the bis(glyoxime)-transition metal complex comprises nickel, copper, or a combination thereof.

Embodiment 7 is a composition according to embodiment 6, wherein the bis(glyoxime)-transition metal complex comprises bis(dimethylglyoximato)-nickel (II).

Embodiment 8 is a colorimetric moisture-indicating sensor comprising: a solid metal oxide support; and a bis (glyoxime)-transition metal complex bound to the support, wherein the visible spectroscopic reflection spectrum of the moisture-indicating sensor changes quantitatively and reversibly according to the amount of moisture in contact with the sensor.

Embodiment 9 is a colorimetric moisture-indicating sensor according to embodiment 8, wherein the bis(glyoxime)-transition metal complex comprises a bis(dimethylglyoximato)-transition metal complex.

Embodiment 10 is a colorimetric moisture-indicating sensor according to embodiment 8, wherein the solid metal oxide comprises an oxide of aluminum, silicon, or a combination thereof.

Embodiment 11 is a colorimetric moisture-indicating sensor according to embodiment 8, wherein the bis(glyoxime)-transition metal complex has a square-planar configuration.

Embodiment 12 is a colorimetric moisture-indicating sensor according to embodiment 8, wherein the solid metal oxide support comprises aluminum or silicon and the bis (glyoxime)-transition metal complex comprises bis(dimethylglyoximato)-nickel (II).

Embodiment 13is a colorimetric moisture-indicating sensor according to embodiment 8, wherein the amount of moisture in contact with the sensor is determined by measuring the visible spectroscopic reflection spectrum of the sensor.

Embodiment 14 is a colorimetric moisture-indicating sensor according to embodiment 13, wherein the sensor quantitatively changes reflection spectrum in the wavelength range of 460 nm to 560 nm.

Embodiment 15 is a colorimetric moisture-indicating sensor according to embodiment 14, wherein the sensor quantitatively changes Hue number.

Embodiment 16 is a method of detecting moisture comprising: providing a composition, the composition comprising: a solid metal oxide support; and a bis(glyoxime)-transition metal complex bound to the support, wherein the visible spectroscopic reflection color intensity change of the composition is quantitative and reversible according to the amount of moisture in contact with the composition; and exposing the composition to a moist atmosphere.

Embodiment 17 is a method of detecting moisture according to embodiment 16, wherein the bis(glyoxime)-transition metal complex comprises a bis(dimethylglyoxime)-transition metal complex.

Embodiment 18 is a method of detecting moisture according to embodiment 16, further comprising measuring the visible spectroscopic reflection spectrum of the composition after exposing the composition to a humid atmosphere.

Embodiment 19 is a method of detecting moisture according to embodiment 16, wherein the solid metal oxide support comprises aluminum, the bis(dimethylglyoxime)-transition metal complex comprises nickel, and the visible spectroscopic reflection color intensity change is measured by reflection spectroscopy in the wavelength range of 460 nm to 560 nm.

Embodiment 20 is a method of detecting moisture according to embodiment 19, wherein the visible reflection spectroscopic color intensity change intensity change is measure by the change in the Hue number.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows. All references cited in this disclosure are herein incorporated by reference in their entirety.

What is claimed is:

1. A method of detecting moisture comprising:
   providing a composition, the composition comprising:
      a solid metal oxide support; and
      a bis(glyoxime)-transition metal complex bound to the support,
   wherein a visible spectroscopic reflection color intensity change of the composition is quantitative and reversible according to an amount of moisture in contact with the composition; and
   exposing the composition to a moist atmosphere.

2. A method of detecting moisture according to claim 1, wherein the bis(glyoxime)-transition metal complex comprises a bis(dimethylglyoxime)-transition metal complex.

3. A method of detecting moisture according to claim 1, further comprising measuring the visible spectroscopic reflection spectrum of the composition after the exposing the composition to the moist atmosphere.

4. A method of detecting moisture according to claim 1, wherein the solid metal oxide support comprises aluminum, wherein the bis(glyoxime)-transition metal complex comprises a bis(dimethylglyoxime)-transition metal complex, wherein the bis(dimethylglyoxime)-transition metal complex comprises nickel, and the visible spectroscopic reflection color intensity change is measured by reflection spectroscopy in a wavelength range of 460 nm to 560 nm.

5. A method of detecting moisture according to claim 4, wherein the visible reflection spectroscopic color intensity change is measure by a change in a Hue number.

* * * * *